United States Patent [19]

Ek et al.

[11] Patent Number: 5,607,695
[45] Date of Patent: Mar. 4, 1997

[54] PROCESS FOR THE MANUFACTURE OF POROUS CELLULOSE MATRICES

[75] Inventors: Bo R. Ek, Stockholm; Kjell G. Eriksson, Spånga; Per Gustaf H. Nyqvist, Tullinge; Gert A. Ragnarsson, Bro, all of Sweden

[73] Assignee: Pharmacia & Upjohn AB, Stockholm, Sweden

[21] Appl. No.: 364,080

[22] PCT Filed: Jun. 5, 1991

[86] PCT No.: PCT/SE91/00396

§ 371 Date: Nov. 30, 1992

§ 102(e) Date: Nov. 30, 1992

[87] PCT Pub. No.: WO91/18590

PCT Pub. Date: Dec. 12, 1991

Related U.S. Application Data

[63] Continuation of Ser. No. 952,831, Nov. 30, 1992, abandoned.

[30] Foreign Application Priority Data

Jun. 6, 1990 [SE] Sweden .................................. 9002017

[51] Int. Cl.$^6$ .................................. A61K 9/10; A61K 9/16; A61K 9/22; A61K 47/38
[52] U.S. Cl. ................ 424/468; 424/488; 424/499; 424/490; 424/495; 424/497; 424/498; 264/15; 428/402
[58] Field of Search .................................. 424/484, 488, 424/495, 497, 498, 490, 494, 468; 514/951; 428/402, 403, 407; 430/107; 502/8; 427/212; 264/7, 15

[56] References Cited

U.S. PATENT DOCUMENTS

| | | | |
|---|---|---|---|
| 3,297,806 | 1/1967 | Battista et al. | 264/129 |
| 4,055,510 | 10/1977 | Peska et al. | 536/57 |
| 4,090,022 | 5/1978 | Tsao et al. | 435/179 |
| 4,138,475 | 2/1979 | McAinsh et al. | 424/494 |
| 4,269,859 | 5/1981 | Morse | 424/362 |
| 4,806,360 | 2/1989 | Leong et al. | 424/486 |
| 4,808,413 | 2/1989 | Joshi et al. | 424/489 |
| 4,900,558 | 2/1990 | Barry et al. | 424/494 |
| 5,049,394 | 9/1991 | Howard et al. | 424/494 |

FOREIGN PATENT DOCUMENTS

| | | |
|---|---|---|
| 0270305A3 | 6/1988 | European Pat. Off. . |
| 0270305A2 | 6/1988 | European Pat. Off. . |
| 0303259A3 | 2/1989 | European Pat. Off. . |
| 0303259A2 | 2/1989 | European Pat. Off. . |
| 1575700 | 9/1980 | United Kingdom . |

OTHER PUBLICATIONS

English Abstract of Japanese 89–1272643 (Oct., 1989).
Bogentoft, et al., Influence of Food on the Absorption of Acetylsalicylic Acid from Enteric–Coated Dosage Forms, Europ. J. Clin. Pharmacol. 24, 351–355 (1978), pp. 351–355.
Ragnarsson, et al., Coated Drug Cores in Multiple Unit Preparations Influence of Particle Size, Drug Development and Industrial Pharmacy, 14(15–17), 2285–2297 (1988).
Battista, Hydrolysis and Crystallization of Cellulose, Industrial and Engineering Chemistry, vol. 42(3), pp. 502–507.
Nystrom, et al., Measurement of axial and radial tensile strength of tablets and their relation to capping, Acta Pharm. Suec. 15, 226–232 (1978).

Primary Examiner—Edward J. Webman
Attorney, Agent, or Firm—Pollock, Vande Sande & Priddy

[57] ABSTRACT

A process for the manufacture of porous cellulose particles, which have regular shape, and a capacity of sorbing 1.5–9 times of their own weight of water, a tap bulk density of less than 0.85 g/ml is provided. The process for the manufacture of these porous cellulose matrices is performed by mechanically treating of hydrolyzed cellulose in a wet stage. The cellulose matrices have preferably a size of at least 0.1 mm and a tap bulk density of 0.1–0.7 g/ml. A bioactive substance or bioactive substances could be sorbed, precipitated or sublimized into the porous structure of the matrices. The matrices can be admixed with drugs or drug containing granules in order to improve the tabletting and tablet properties and thereafter compressed.

Drug loaded matrices can be used for direct compression of tablets.

30 Claims, No Drawings

PROCESS FOR THE MANUFACTURE OF POROUS CELLULOSE MATRICES

This application is a continuation of Ser. No. 07/952,831 filed on Nov. 30, 1992 now abandoned.

BACKGROUND

1. Field of the Invention

The present invention is related to a process for the manufacturing of new multiple unit carriers and release controlling systems for bioactive materials as well as the manufacturing of a new additive to be used in the formation of tablets and especially in direct compression and to obtain multiple unit preparations in the form of compressed and disintegrating tablets.

2. Background of the Invention

This invention relates to the administration or dispersion of bioactive materials in the form of small discrete particles, often referred to as multiple unit (MU) preparations or systems. It is well known that MU systems offer several advantages such as good dosing and handling properties as well as excellent possibilities to obtain a controlled release of the active ingredient, or ingredients.

The control of the release rate, or other release properties, can be achieved in a number of different ways such as using hydrophobic and or hydrophilic materials in which the bioactive material is embedded and released by a diffusion or erosion process as well as coating particles (crystals, beads, pellets etc.) with a release controlling barrier.

The barrier may be designed e.g. to control the release rate by diffusion- or osmotic processes or to delay the release by a controlled disintegration of the barrier, which may be designed to be affected by environmental conditions such as humidity, pH, microorganisms or enzymes.

The above mentioned release controlling systems have been of special importance within the pharmaceutical field during the last decades. Apart from the possibilities to control the delivery of drugs to humans or creatures, and thus to obtain therapeutical advantages for a large number of drugs, several advantages with MU preparations compared to single unit preparations have been described in the literature.

It is, for example, possible to obtain a more reproducible emptying of small units (e.g. less than 1–2 mm, c.f. Bogentoft C et al, Influence of food on the absorption of acetylsalicylic acid from enteric coated dosage forms, Europ. J. Clin. Pharmacol. (1978), 14, 351–355) and thus a dispersion over a large area of the gastrointestinal canal. This may promote the absorption process, causing reduced variability, as well as reduced local irritation in the oesophagus or other parts of the gastrointestinal tract.

A large number of processes have been developed to produce the MU cores. The cores may include release retarding components, be intended for further processing such as coating with suitable materials or may simply act as a carrier for the active material. The processes includes for example controlled crystallization and mechanical formation of spherical particles from mixtures of active substances and hydroplastic additives as well as spray drying and spray chilling processes. There are numerous ways to form spherical small particles by mechanical processes, e.g. by using coating drums, pans and extrusion/spheronization and fluid bed equipment (Pharmaceutical Pelletization Technology, Ed. I Ghebre Sellassie, Marcel Dekker, Inc New York 1989).

It is, in general, very critical to get particles of a well defined size, form and surface area (Ragnarsson and Johansson, ref. Drug Dev. Ind. Pharm. 14, 2285 (1988) in order to obtain good handling properties, good dose uniformity or accurate control of the release properties. To fulfill these requirements, the production processes are in general complex including several steps and often finished by e.g. a sieving process to obtain uniform particles. A manufacturing process including many steps will be time consuming and expensive but may also pose environmental hazards when handling toxic or irritating substances. Of special importance is the loss of active material in the different production steps and, especially, when sieving materials in order to obtain the required particle size fraction.

The optimal solution would be to produce spherical inert particles of the required particle size and size distribution that can be loaded with the bioactive material, e.g. by sorption into a porous structure, and that optionally may control the release of the bioactive material. It would thus be possible to reduce the number of production steps and the production costs, to minimize losses of active material during manufacturing and to reduce environmental problems.

It has previously been described (U.S. Pat. No. 3,297,806) that agglomerated cellulose produced by spray drying can be used for loading of substances in order to obtain a chemical stabilization of the substances especially from oxidation. The described procedure does, however, give cellulose agglomerates with a limited sorbing capacity (less than 1.5 times of water of the weight of the cellulose agglomerates according to the examples). The described material is identical with commercial microcrystalline cellulose for tabletting (e.g. Avicel and Dynacel). Furthermore, no mechanical treatment is performed prior to loading of the substance to be stabilized. Fractionation in order to obtain defined particle sizes is, in this case, performed on the loaded agglomerates which lead to reject fractions of undesirable particle sizes containing the loaded substance which in many cases is very costly.

It has also been described that agglomerates can be formed from cellulose derivatives (G. B. Patent 1 575 700) to be used for immobilization of e.g. enzymes through ionic or chemical covalent bonding. However, the carrier system is not built up from pure cellulose and the immobilization of the molecules is not built basically on physical entrapment.

An abstract from Japanese patent application JP 88101288 discloses porous cellulose particles in a crystalline form with fine pores, a porosity higher than 20% and more than 90% over 350 mesh. (=40 micron) which are used as additives for tabletting of drugs and as a carrier. The process disclosed cannot give particles which are regular and which have a high sorbing capacity.

Pharmaceutical products of the MU type are often dispersed in hard gelatin capsules. They may also be dispersed in compressed disintegrating tablets. These types of tablets offer some advantages compared to capsules or sachets such as being an elegant dosage form and giving units that can be divided into two or more dose units or disintegrated in water to make the drug easier to swallow.

The production of tablets based on barrier coated MU-cores is however associated with some special problems. To protect the coating layer from being disrupted during compression, it is in general necessary to add materials with good bonding properties that will aid in the formation of tablets as well as to protect the coating layer. The material should preferably have suitable plastic properties, i.e., be easily deformed and form strong compacts at low pressure. Such typical material is microcrystalline cellulose, available on the market under the trade names of, for example, Avicel (FMC Corp.), Emcocel (Finn Sugar, Finland) and Dynacel (Cellupharm AB, Sweden). Although these materials have outstanding compaction properties, as discussed above, they are not ideal as additives for compressed MU preparations. The main drawback is that they differ considerably in form, size and size distribution from MU cores. As the MU cores in general are spherical particles in the particle size range of 0.5–1.5 mm, they will form a free flowing material that when mixed with commercially available microcrystalline cellulose qualities will tend to give severe segregation during handling and tabletting and thus poor content uniformity.

The optimal solution would be to use materials of exactly the same size and size distribution as the MU cores but with very good tabletting properties. It is widely recognized that it is extremely difficult to obtain such materials by granulation methods or other conventional pharmaceutical processes, based on microcrystalline cellulose or other pharmaceutically acceptable substances. Materials of the preferred type, i.e., with a well defined particle form and adjustable and narrow particle size as well as excellent compaction properties, would also be of very large general interest in the manufacturing of tablets and especially in direct compression.

OBJECTS OF THE INVENTION

In view of the above presentation, there is an obvious need for further improvements within the area of carrier and release controlling systems for bioactive materials in MU form. There is also a need for good methods to obtain MU preparations in the form of compressed tablets.

It has surprisingly been found that the present invention which is only based on pharmaceutically acceptable constituents, may solve a number of the problems discussed above, i.e., it may reduce the number of production steps and facilitate the production of MU preparations of bioactive materials by reducing the losses of active material during manufacturing, by offering a simple method to control the release of active materials or by giving well defined particles that are very suitable for further processing into modified release systems as well as offering a well defined material, concerning form and size, with excellent compaction properties that is very suitable for the formation of MU preparations in the form of compressed tablets and to be used for a general production of tablets, especially by direct compression.

DESCRIPTION OF INVENTION

The present invention concerns a process to obtain mainly spherical, matrices of cellulose with a well defined particle size, size distribution and porosity. Preferably thereafter these particles are used to obtain multiple units containing bioactive materials, which are incorporated into the matrices in a second step, to control the release of the bioactive material by adjusting the porosity, i.e. the porous diffusion retarding network within the matrices, by including release modifying substances into the matrices or by applying a barrier coating (release modifying membrane) as well as using the cellulose matrices as tabletting additives, especially in the formation of MU preparations in the form of compressed tablets and in direct compression.

The present invention concerns more specifically a process for the manufacture of porous cellulose matrices from hydrolyzed cellulose. The hydrolyzed cellulose is mechanically treated in a wet stage into regular particles having the capacity of sorbing 1.5–9 times of their own weight of water and a tap bulk density of less than 0.85 g/ml.

A soluble additive, such as sodium chloride in solid form could be included together with the cellulose before the mechanical treatment and thereafter dissolved from the matrices in order to further increase the porosity. The cellulose matrices could have a size of at least 0.1 mm and a bulk density of 0.1 to 0.7 g/ml preferably 0.1–0.5 g/ml. In pharmaceutical use the size of the matrices is preferably 0.1–2.0 mm.

A bioactive substance or bioactive substances in a solid, liquid, or semiliquid form, preferably as a solid, solution, suspension, emulsion, oil, super critical fluid or melt, could be sorbed, precipitated or sublimized into the porous structure of the matrices in one or several steps optionally with intermediate drying.

The invention is not only applicable on drugs but also in the production and use of bioactive substances such as herbicides, insecticides and fertilizers especially when a controlled dosing or controlled release is desirable.

The release rate of the bioactive material could be controlled by adjusting the porosity of the matrices. The adjustment is e.g. done by degree of hydrolysis (see Tables 2–3) or by the mechanical treatment.

The fluid, liquid or semiliquid could contain one or more materials in order to control the release of the bioactive substance. The material for modifying the release is preferably chosen from cellulose derivatives, acrylic acids derivatives, phospholipids, hydrocarbons, carboxylic acids, ethers, ethers or alcohols, and waxes or lipids. The release of the bioactive substance can also be modified by other substances such as surface active agents in order to improve the dissolution rate of sparingly soluble substances and promote solubilization.

The release of the bioactive substance or bioactive substances could be modified by applying a release controlling material on the surface of the spherical particles such as cellulose derivatives such as ethyl cellulose, acrylic acids derivatives and copolymers thereof, hydrocarbons, carboxylic acids, esters, ethers, alcohols and waxes or lipids.

The porous matrices consist, preferably up to 100% of partially hydrolyzed cellulose or have been hydrolized to a level that gives a sedimentation volume of 20–500 ml/10 g, specific 100–300 ml/10 g.

One way of performing the process is that the cellulose is not dried but used as the wet mass obtained from the hydrolysis as such in the formation of the matrices.

Tablets could be prepared by admixing the matrices prior to compaction with drugs, or drug containing granules in order to improve the tabletting and tablet properties or by admixing the matrices prior to compaction with drug containing units of similar size such as pellets, granules or crystals which have been coated to modify the drug release properties, mask unpleasant taste or to improve the stability and thereafter compressed.

When the matrices are loaded with a drug they could be directly compressed into tablets.

When using the invention in the preparation of MU formulations, the basic concept is that the porous matrices of cellulose are formed in a separate process whereafter the drug substance or substances (or other bioactive materials) are incorporated into the matrices in a second step.

The size and size distribution of the final beads are determined in the first manufacturing step while amount of active material to be incorporated is controlled in the second step. The invention makes it possible to vary the amount of active material that can be incorporated but also to control the release rate of the active material as the cellulose network acts as a porous diffusion retarding system. The release properties may also be modified by adding suitable substances, such as polymers and waxes, during or after the incorporation of the active material or finally as a film coat.

The advantages of the present invention are:

1. The porous cellulose matrices can be produced from microcrystalline cellulose, a well documented material used as a pharmaceutical excipient (USP XXII).
2. The porous cellulose matrices can be given a spherical shape and the particle size distribution can be controlled and determined before the drug substance is incorporated. A minimum amount of beads having a wrong size are obtained thereby eliminating the need to fractionate the final beads. This is particulary important for expensive drug substances and for active substances that may cause environment hazards during dust-forming processes due to toxic or irritating properties.
3. The high porosity of the cellulose matrices enables loading of substances up to 9 times the weight of the empty matrices.
4. Matrices according to 2 offer excellent materials for further processing into modified release preparations by conventional coating procedures.
5. The matrices are mechanically resistant and keep their shape at soaking in water or organic solvents and drying during agitation in e.g. fluid bed equipment. The matrices are mechanically resistant also to combinations of these types of processes.
6. The matrices as such, or after addition of release modifying substances, can be used to obtain modified release preparations. This offers a considerable reduction in the number of production steps and in production costs when compared to most other methods to produce MU preparations with a controlled release of the active material.
7. The matrices have excellent compaction properties and since the particle form, size and size distribution can be controlled, they have outstanding properties for the production of MU-preparations in the form of compressed tablets. They have, with or without drug load, also excellent properties for a general production of tablets, especially by direct compression.
8. The matrices can be used as an aid in the synthesis of chemical compounds where the compound will precipitate in the porous structure of the matrices. This is of value especially for substances which precipitate in a semi solid or liquid form or are tacky at handling. For bioactive materials to be compressed e.g. into tablets, the loaded matrices can be directly compressed.

CELLULOSE

Cellulose is a hydroplastic material, i.e. it can be softened by wetting with water which enables it to be formed to a desired shape by mechanical treatment. The cellulose fibre is built up by fibrils with the typical size 0.1×0.3 mm. The fibrils in turn is built up by microfibrils with the typical size 0.1–50 µm. Each microfibril consists of cellulose chains with a more or less pronounced long range order (crystalline to amorphous). The cellulose chains are bound together in two directions and these planes build up a lameliar structure. The length of the cellulose chains varies between different plant species but is typically around 10,000 cellulose (sugar) units. This is defined as the degree of polymerization (DP= 20,000). (Battista O. A., Industrial and Engineering Chemistry 1950, (42) 502).

When purifying cellulose the length of the cellulose chains is shortened. Typical cellulose pulp for paper manufacture has a DP around 2000 while the microcrystalline cellulose used as a pharmaceutical excipient has a DP around 100.

Cellulose is commercially available as natural fibre (20× 2000 µm) and in a degraded form (1×100 µm). In the latter material the amorphous regions of the cellulose have been removed by hydrolysis and the fibrous structure eliminated by mechanical treatment. The hydrolysis is performed e.g. at low pH and high temperature. The degree of hydrolysis can be regulated by e.g. the reaction time. The degree of polymerization (DP) reaches an end value during the hydrolysis which is designated as LODP (Leveling of Degree of Polymerization), (Battista O. A., Industrial and Engineering chemistry 1950, (42) 502). Microcrystalline cellulose has been obtained by hydrolysis to LODP and can be compressed, e.g. to tablets.

CHARACTERIZATION OF CELLULOSE

The cellulose used for producing the porous spherical matrices can be characterized by the following method as a measure of the degree of polymerization:

10.00 g of dry cellulose (water content not more than 5%, w/w, measured as loss on drying, 105° C., 3h) is suspended in 500 ml of water with a high shear mixer. The suspension is mixed for 10 s and another 500 ml water is added. Mix again for 10 s and pour the suspension into a 1000 ml measuring cylinder. Put the measuring cylinder on a horizontal plane, wait 1 h and read the sediment volume in ml.

In Table 1 is the sedimentation volume and DP-number for celluloses used to produce porous spherical matrices given. The four cellulose examples No. I, No II, No. III and No. IV have been hydrolyzed to different degrees of hydrolysis by different reaction time.

TABLE 1

Sedimentation volume and DP-number for celluloses used to produce porous spherical matrices.

| Cellulose | Sedimentation Volume (ml) | DP-number |
|---|---|---|
| AVICEL PH 101 a) (FMC, Corp. USA) | 45 | 142 |
| Emcocel a) (Finn Sugar, Finland) | 55 | — |
| Dynacel a) (Cellupharm, Sweden) | 50 | 105 |
| Cellulose fibres No. I b) (short hydrolysis) | 130 | 107 |
| Cellulose fibres No. II b) (short hydrolysis) | 265 | 121 |
| Cellulose fibres No. III b) (short hydrolysis) | 280 | 137 |
| Cellulose fibres No. IV b) (short hydrolysis) | 410 | 143 | a) Commercially available microcrystalline cellulose.
b) Commercially available cellulose pulp hydrolyzed to different degrees.

CELLULOSE MATRICES

In the present invention porous matrices of regular shape (e.g. rod shaped or preferably spherical) in the size range 0.1–2.0 mm (especially 0.3–1.5 mm) are described. This means that the cellulose which is building up these beads should consists of fibres (fibre pieces) in the same size range as the diameter of the final matrices. Common cellulose pulp fibres are difficult to handle due to its fluffy structure which gives the final matrices a hairy surface structure.

It has been found in the present invention that by controlling the degree of hydrolysis and also the mechanical treatment (manufacturing process), it is possible to obtain desirable and reproducible properties of the matrices. The degree of hydrolysis has been used as the main controlling factor but as the manufacturing process (see e.g. Table 2) will also influence the properties, it may be possible to use the commercial microcrystalline cellulose. This is especially the case in manufacturing example 2 below. It has been established that a hardening of the surface of the cellulose fibres occurs at drying which decrease the plasticity of the cellulose (Kungliga Tekniska Högskolan, Stockholm, Sweden. Compendia in Paper Technology, 1986–87). Thus, it is an advantage if the cellulose can be taken directly from the hydrolysis into the matrix forming process without intermediate drying. This undried cellulose has a large bonding surface which results in stronger matrices. However, it is possible as a first step in the process of forming the porous matrices to moisten dry cellulose with approximately 0.5–0.9 times of the dry weight with water.

The process of forming the porous spherical matrices can be performed by different types of mechanical treatment of the wet, cellulose fibres, e.g. extrusion under pressure, high shear mixing, rolling on a rotating disc, in a rotary dryer. Two main routes have been identified.

1. The wet hydrolyzed cellulose is charged into a rotating mixer for wet massing and then extruded before charging into a spheronization device, where the final forming and, optionally, drying is performed by means of controlled air velocity, temperature and gravitational forces.

It is also possible to extrude this wet cellulose directly for the final forming and drying.

2. The wet hydrolyzed cellulose is mixed with a particulate soluble additative, before eventual extrusion, final forming and drying. The additive is then washed away with a solvent, e.g. water, and the porous spherical matrices are dried. In order to control that all additive hase been washed away, salts like sodium chloride are especially useful as additative they can easily be detected by conductivity measurements. By incorporating soluble additative of different amounts and particle size distributions it is possible to control the pore size and shape in the final porous spherical matrices.

The tap bulk density (DIN 53194), i.e. the porosity, of the formed matrices is dependent and adjusted by using cellulose that has been hydrolysed to different degrees characterised e.g. by the sedimentation volume as discussed above. Also the mechanical treatment of the fibres during manufacturing of the fibres will have some influence.

TABLE 2

| Sediment volume, ml/10 g, of the cellulose fibres | Tap bulk density g/ml Mechanical treatment* | |
|---|---|---|
| | I | II |
| 50 | 0.83 | 0.60 |
| 120 | 0.77 | 0.52 |
| 200 | 0.63 | 0.50 |
| 280 | 0.52 | 0.36 |
| 410 | 0.47 | 0.28 |

*I = wet mixing prior to spheronization
II = wet mixing and extrusion

As the bulk density are proportional to the porosity of the matrices, the variables according to Table 2 and in particular the sediment volume, and thus the degree of hydrolysis (cf. Table 1), are used to obtain the high absorbing capacity of the matrices and also to control this capacity (Table 3). To obtain a very high absorbing capacity, process route No. II is used e.g. with sodium chloride as soluble excipient for the matrix formation.

TABLE 3

| Tap bulk density of the matrices, g/ml | Absorption capacity g water/g dry matrices |
|---|---|
| 0.85 | 1.9 |
| 0.83 | 2.0 |
| 0.82 | 2.1 |
| 0.69 | 2.2 |
| 0.63 | 2.4 |
| 0.60 | 2.5 |
| 0.58 | 2.5 |
| 0.50 | 2.9 |
| 0.42 | 3.1 |
| 0.40 | 3.3 |
| 0.36 | 3.5 |
| 0.35 | 3.6 |
| 0.29* | 4.0 |
| 0.28* | 4.2 |
| 0.21* | 5.0 |
| 0.18* | 5.0 |
| 0.17* | 6.2 |
| 0.16* | 6.5 |

*Process route No. II

The chemical characterization of the porous spherical matrices produced from any of the cellulose qualities in Table 2 conforms with the purity limits given in Table 4 (pharmacopeial grade).

TABLE 4

| Purity characteristics of porous spherical matrices | |
|---|---|
| Dry substance | Min. 95% (w/w) |
| Water soluble substances | Max. 0.10% |
| Residue on ignition | Max. 0.05% |
| Heavy metals | Max. 0.001% |
| pH | 5,5–7,0 |
| Microbiological contamination | Max. 100 microorganisms per gram |

Production of Porous Matrices of Spherical Shape

EXAMPLE 1

Moist hydrolyzed cellulose No. III (sediment volume 280 ml/10 g) (500 g, approx. 50% w/w water) and water (501 g) was mixed in a planetary mixer for approximately 10 minutes.

The moist cellulose was extruded through a 2 mm screen, followed by a 2.38 mm hand screen.

The extruded moist cellulose was spheronized in batches (approx. 200 ml) in a stainless steel rotary dryer (diameter 30 cm). The normal spheronization time was 5 to 8 minutes.

After the spheronization, the porous matrices were dried on trays (+80° C., 3 hours).

Weight 224 g Bulk density 0.35 g/ml.

TABLE 5

| Size class (mm) | Cumulative size (%) |
|---|---|
| >1.40 | 100 |
| 1.40–1.18 | 99.3 |
| 1.18–1.00 | 97.6 |

TABLE 5-continued

| Size class (mm) | Cumulative size (%) |
|---|---|
| 1.00–0.85 | 92.7 |
| 0.85–0.71 | 82.3 |
| 0.71–0.50 | 67.8 |
| 0.50–0.36 | 35.3 |
| 0.36–0.25 | 10.2 |
| <0.25 | 3.2 |

EXAMPLE 2

Moist hydrolyzed cellulose (Dynacela), (sediment volume 50 ml/10 g) (100 g, approx. 50% w/w water) and water (20 g) was mixed in a planetary mixer for approximately 10 min.

The extruded cellulose was spheronized in a stainless steel rotary dryer in accordance with Example 1 above.

After spheronization, the porous matrices were dried on trays (+80° C., 3 hours).

Weight 45 g Bulk density 0.83 g/ml.

Table 6 shows the particle size distribution (sieve analysis).

TABLE 6

| Size class (mm) | Cumulative under size (%) |
|---|---|
| >1.40 | 100 |
| 1.40–1.18 | 98.0 |
| 1.18–0.85 | 88.0 |
| 0.85–0.50 | 76.5 |
| 0.50–0.25 | 31.0 |
| 0.25–0.10 | 5.0 |
| <0.10 | 0 |

EXAMPLE 3

Moist hydrolyzed cellulose N. III (sediment volume 280 ml/10 g) (100 g, approx. 50% w/w water) and water (20 g) was mixed with sodium chloride (43 g) in a planetary mixer for approximately 5 min.

The moist cellulose/sodium chloride mixture was extruded through a 2 mm screen.

After spheronization the cellulose/sodium chloride beads were dried on trays (+80° C., 3 hours).

The dried beads were then washed with water in 100 ml portions 5 times in a glass beaker and thereafter dried on trays (+80° C., 3 hours).

Weight 41 g Bulk density 0.17 g/ml.

TABLE 7

| Sieve class (mm) | Cumulative under size (%) |
|---|---|
| >1.40 | 100 |
| 1.40–1.18 | 86.0 |
| 1.18–0.85 | 75.9 |
| 0.85–0.50 | 68.0 |
| 0.50–0.25 | 39.0 |
| 0.25–0.10 | 10.0 |
| <0.10 | 0 |

Incorporation of Substances

EXAMPLE 4

Potassium chloride 5.0 g (67 mmol) was dissolved in 30 g water. The solution was poured on 10.1 g cellulose matrices from Example 1 under gentle mixing and heating.

The moist matrices were dried in hot air. The drying was continued until the material was dry i.e. had a water content of less than approximately 5%. The final matrices contained 64% (w/w) potassium chloride and showed a density of 0.59 g/ml.

EXAMPLES 5–10

Substances according to the Table 8 below were incorporated as solutions in water or ethanol in a similar way as described in Example 4.

TABLE 8

| Example | Substance | Cellulose matrices with a density of (g/ml) | Solvent | % active substance after incorporation |
|---|---|---|---|---|
| 5. | N-acetyl cysteine | 0.16 | water | 62 |
| 6. | N-acetyl cysteine | 0.16 | ethanol | 60 |
| 7. | N-acetyl cysteine | 0.35 | water | 55 |
| 8. | N-acetyl cysteine | 0.35 | ethanol | 55 |
| 9. | Furosemide | 0.35 | alkaline water | 51 |
| 10. | Furosemide | 0.35 | ethanol | 56 |

EXAMPLE 11

35 g paraffin oil was poured on 100 g cellulose matrices from Example 1, particle size 0.8–1.0 mm, in a beaker. The oil was added in two portions (25+10 g). The final matrices were well moistened (loaded) with the oil (26% w/w) without being tacky.

Incorporation of Substances to Control the In Vitro Release Properties

EXAMPLE 12

Isosorbide dinitrate (ISDN) was dissolved in acetone and added to cellulose matrices, from Example 1 and a particle size of 1.0–1.4 mm, at 40° C. in accordance with Example 4.

The acetone was evaporated in a rotary evaporator to give free-flowing dry particles with a ISDN content of 29% w/w.

The table 9 below shows the in-vitro dissolution rate of ISDN at 37° C. in water (mean values, n=5) using the USP XXI paddle apparatus at 75 rpm.

TABLE 9

| Time | % Released mean | C.V.a) |
|---|---|---|
| 30 | 29 | 7.7 |
| 60 | 42 | 7.5 |
| 120 | 58 | 6.7 |
| 240 | 78 | 5.4 |
| 300 | 85 | 4.8 |

TABLE 9-continued

| Time | % Released mean | C.V.a) |
|---|---|---|
| 360 | 90 | 4.3 |
| 420 | 93 | 3.9 | a)Coefficient of Variation

ISDN incorporated in conventional tablets (e.g. Sorbangil [R] tabl., KABI) is released almost instantaneously.

EXAMPLE 13

Terodiline and n-hexadecane (10:2 w/w), were dissolved in dichloromethane and coated on cellulose matrices, from Example 1 and particle size of 1.0–1.4 mm. The dichloromethane was evaporated in a rotary evaporator.

The Table 10 below shows the in-vitro dissolution rate of terodiline from terodiline-loaded cellulose matrices with and without the release retarding agent (n-hexadecane) USP XXI Paddle apparatus 50 rpm, chloride buffer pH 1.2, 37° C.

TABLE 10

| | % terodiline released from | |
|---|---|---|
| Time, min | matrices including n-hexadecane | matrices without n-hexadecane |
| 0 | 0 | 0 |
| 1 | 3 | 7 |
| 5 | 44 | 61 |
| 10 | 64 | 82 |
| 15 | 77 | 93 |
| 20 | 85 | 98 |
| 30 | 95 | 100 |
| 40 | 99 | 100 |
| 60 | 100 | 100 |

EXAMPLE 14

Potassium chloride loaded cellulose matrices were prepared according to Example 4.

The matrices were coated in a laboratory scale fluid-bed coater (NICA) with a ethylcellulose latex in water (Ethocel AQ, Colorcon Ltd.). The amount of ethylcellulose applied was approximately 15% (w/w).

The Table 11 below shows the in-vitro dissolution of potassium chloride from coated and uncoated matrices respectively.

(USP XXI paddle method, 271†C, 50 rpm, phosphate buffer pH 6.8 (mean of 2 samples)).

TABLE 11

| | % Potassium chloride released from | |
|---|---|---|
| Time, min. | coated particles | uncoated particles (reference) |
| 30 | 32 | 100 |
| 60 | 61 | — |
| 120 | 84 | — |
| 180 | 93 | — |
| 240 | 95 | — |

EXAMPLE 15

Cellulose matrices (1.0–1.4 mm) produced according to Example 12 containing 29% (w/w) isosorbide dinitrate (ISDN)(10 g) and nonpareil-beads (0.7–0.85 mm) (400 g) were coated in a fluid-bed coater.

The film solution was prepared from ethylcellulose (37 g), hydroxypropylmethylcellulose (8 g), triethylcitrate (5 g), ethanol (99.5%)(500 g) and dichlormethane (750 g).

After coating, the cellulose matrices were dried and sieved (1.0 mm) and resulted in free flowing spherical shaped particles.

This example shows that the matrices kept fluid physical properties during processing.

The Table 12 below shows the in-vitro dissolution rate of ISDN from coated matrices. USPXXI paddle method, 37° C., 75 rpm, water.

TABLE 12

| Time (minutes) | Rate (% ISDN released per hour) |
|---|---|
| 30 | 4.0 |
| 60 | 3.0 |
| 120 | 2.4 |
| 180 | 2.0 |

Incorporation of Substances by Precipitation

EXAMPLE 16

Furosemide, 10.0 g (30 mmol) was dissolved in 245 ml methanol at about 30° C. in a 500 ml Erlenmeyer-flask. 40.0 g cellulose matrices from Example 1 was added to the clear solution and shaked gently by hand for approximately 30 seconds.

After 15 minutes 10 ml water was added to the flask and thereafter the flask was left standing in room temperature over night.

10 ml water was then added and the flask was shaked gently by hand and stored in room temperature for about 8 hours. 5 ml water was added followed by gentle agitation and the flask was left standing in room temperature over night.

The flask was thereafter placed in a refrigerator and kept at about +5° C. for 4 days.

The matrices, now including furosemide, were filtered off.

The moist matrices were transferred to a 250 ml evaporation flask and dried on a vacuum rotary evaporator at approximately 45° C. and rotation speed of 20 rpm. The matrices were free-flowing after approximately 10 minutes. The rotation speed was set to approximately 10 rpm. Total drying time was 2.5 hours.

Yield of dried matrices: 46.2 g.

Tabletting of Matrices

EXAMPLE 17

Tablets were compressed in an instrumented single punch machine (Korsch EKO, West Germany). A weighed amount of cellulose was manually filled into the die (diameter 1.13 cm) and tablets were compressed at 30 rpm to a constant thickness at maximum pressure. The load was varied by varying the amount of fill.

Directly after compaction the thickness and weight of the compacts were measured and the tablets were stored 14 hours before mechanical strength testing (Nyström C., Malmqvist K., Mazur J., Alex W., Hölzer A. W. Acta Pharm. Suec. 15, 226 (1978)) in both axial and radial direction.

Table 13 below summarizes the mechanical strength in both axial and radial direction obtained at various compaction pressure for both commercial microcrystalline cellulose and porous cellulose matrices from Example 1.

TABLE 13

| Compaction pressure kp/cm2 | Tablet thickness (cm) | Tablet weight | Dynacel[R1)] radial (N) | Dynacel[R1)] axial (N) | Cellulose matrices[2)] radial (N) | Cellulose matrices[2)] axial (N) |
|---|---|---|---|---|---|---|
| 40 | 0.348 | 0.385 | 95 | | | |
| 57 | 0.344 | 0.435 | 152 | | | |
| 68 | 0.352 | 0.457 | 201 | | | |
| 100 | 0.361 | 0.508 | 305 | | | |
| 27 | 0.345 | 0.334 | | 23 | | |
| 38 | 0.347 | 0.375 | | 52 | | |
| 88 | 0.250 | 0.493 | | 143 | | |
| 124 | 0.367 | 0.536 | | 197 | | |
| 26 | 0.340 | 0.286 | | | 16 | |
| 60 | 0.343 | 0.372 | | | 100 | |
| 100 | 0.348 | 0.425 | | | 185 | |
| 128 | 0.352 | 0.449 | | | 224 | |
| 40 | 0.365 | 0.338 | | | | 15 |
| 48 | 0.341 | 0.346 | | | | 46 |
| 140 | 0.366 | 0.460 | | | | 62 |
| 180 | 0.380 | 0.496 | | | | 110 |

[1)]Microcrystalline cellulose of commercial quality.
[2)]Porous cellulose matrices from Example 1.

Tabletting of Matrices Containing Substances

EXAMPLE 18

Tablets were compressed in a single punch machine (Diaf model TM20 Denmark). A weighed amount of matrices from Example 16 was manually filled into the die (diameter 10 mm) and tablets were compressed at a low speed at three different pressures. The load was varied by varying the depth of the punch strike.

Reference tablets were made from dry-mixed microcrystalline cellulose (Avicel® PH101, FMC Corp.) and furosemide in the same proportions as in the matrices from Example 16.

The reference tablets were compressed at the same pressures as the matrice tablets.

The Table 14 below summarizes mechanical strength in radial direction (mean values of 3 tablets, Schleuniger model THP-4M).

TABLE 14

| Tablet | Height (mm) | Weight (g) | Mechanical strength (kp) |
|---|---|---|---|
| 65 kp/cm² | 3.92 | 0.34 | 14.8 |
| 80 kp/cm² | 3.88 | 0.35 | 16.5 |
| 100 kp/cm² | 3.80 | 0.34 | 19.6 |
| Reference tablets (Avicel[R] furosemide | | | |
| 65 kp/cm² | 3.96 | 0.34 | >limit (50 kp) |
| 80 kp/cm² | 3.80 | 0.34 | >limit (50 kp) |
| 100 kp/cm² | 3.79 | 0.34 | >limit (50 kp) |

EXAMPLE 19

Extended release pellets (0.7–1.0 mm diameter) containing isosorbide dinitrate and covered by a film to control the release-rate were mixed with empty cellulose matrices (0.7–1.0 mm diameter) made according to Example 1.

The mixture was compressed to tablets in an instrumented single-stroke tablet-machine at 150±10 MPa.

The release of isosorbide dinitrate was examined in a dissolution bath (USP XXI paddle, 37° C., distilled water, 150 rpm).

In table 15 dissolution data from the uncompressed pellets (A), the tablets containing pellets and empty cellulose matrices (B) and the tablets containing compressed isosorbide dinitrate-pellets (C) are presented.

TABLE 15

| | Percent isosorbide dinitrate dissolved | | |
|---|---|---|---|
| Time (min.) | A | B | C |
| 30 | 5.8 | 13.5 | 3.7 |
| 60 | 12.6 | 25.0 | 6.7 |
| 120 | 26.8 | 44.3 | 11.4 |
| 240 | 52.6 | 72.3 | 18.5 |
| 500 | 93.8 | 101 | 29.2 |

A = Pure extended release isosorbide dinitrate-pellets
B = Tablets containing 25% isosorbide dinitrate-pellets and 75% empty cellulose matrices
C = Tablets containing only isosorbide dinitrate-pellets This example shows that the tablets according to our invention (B) give a dissolution which is comparable to the dissolution from the isosorbide dinitrate-pellets per se (A).

We claim:

1. Process for the manufacture of porous cellulose matrices characterized by that hydrolyzed cellulose that has been degraded by hydrolysis to a level that gives a sedimentation volume of 150–500 ml/10 g is mechanically treated by spheronization in a wet stage into spherical particles having a capacity of sorbing 1.5–9 times of their own weight of water and a tap bulk density of 0.1–0.7 g/ml in the dry state.

2. A process according to any of claims 1 wherein said cellulose matrices have a size of at least 0.1 mm.

3. Process according to claim 1 characterized by that the cellulose is used as the wet mass obtained from the hydrolysis as such in the formation of the matrices.

4. The process of claim 1 wherein said capacity of sorbing is 3–7 times.

5. The process of claim 1 wherein said tap bulk density is 0.1–0.5 g/ml.

6. The process of claim 1 wherein said porous matrices are 100% hydrolyzed cellulose.

7. The process of claim 1 wherein said sedimentation volume is 300–500 ml/10 g.

8. Porous cellulose matrices that has been degraded by hydrolysis to a level that gives a sedimentation volume of 150–500 ml/10 g characterized in that they are manufactured from hydrolyzed cellulose by mechanical treatment by spheronization in a wet stage into spherical particles with a sorbing capacity of 1.5–9 times of their own weight of water and a tap bulk density of 0.1–0.7 g/ml in the dry state.

9. Porous cellulose matrices according to claim 8 characterized in that a water soluble additive is mixed with cellulose before the mechanical treatment and thereafter dissolved from the matrices in order to further increase the porosity.

10. Porous cellulose matrices according to claim 8 characterized in that the matrices have a size of at least 0.1 mm.

11. Porous cellulose matrices according to claim 8 characterized in that they contain at least one bioactive substance in a solid, liquid or a semi-solid form.

12. Porous cellulose matrices according to claim 11 wherein the porosity of the matrices is adjusted by degree of hydrolysis or by mechanical treatment to control the release of the bioactive compound and that the solid, liquid or semiliquid contain one or more release controlling materials capable of modifying the release rate of the bioactive compound or compounds selected from the group consisting of esters, ethers, alcohols and waxes.

13. Porous cellulose matrice according to claim 12 characterized in that a release controlling material selected from the group consisting of esters, ethers, alcohols and waxes is applied to the surface of the spherical matrices particles.

14. Porous cellulose matrices according to claim 11 characterized in that the porosity of the matrices is adjusted by degree of hydrolysis or by mechanical treatment to control the release of the bioactive compound and in that the solid, liquid or semiliquid contain one or more release controlling materials capable of modifying the release rate of the bioactive compound or compounds selected from the group consisting of cellulose derivatives, acrylic acid derivatives and co-polymers thereof, carboxylic acids, and lipids.

15. Porous cellulose matrices according to claim 14 characterized in that a release controlling material selected from the group consisting of cellulose derivatives, acrylic acid derivatives, carboxylic acids, and lipids is applied to the surface of the spherical matrices particles.

16. The matrices of claim 8 wherein said sorbing capacity is 3–7 times.

17. The matrices of claim 8 wherein tap bulk density of said matrices is 0.1–0.5 g/ml.

18. The matrices of claim 8 wherein said sedimentation value is 300–500 ml/10 g.

19. The matrices of claim 7 consisting of 100% of hydrolyzed cellulose.

20. Process for the manufacture of porous cellulose matrices characterized by that sodium chloride is mixed with hydrolyzed cellulose before mechanical treatment by spheronization in a wet stage into spherical particles having a capacity of sorbing 1.5–9 times of their own weight of water and a tap bulk density of less than 0.85 g/ml in the dry state, whereupon the sodium chloride is dissolved from the matrices in order to further increase the porosity, and wherein said hydrolyzed cellulose has been degraded by hydrolysis to a level that gives a sedimentation volume of 150–500 ml/10 g.

21. Process for the manufacture of porous cellulose matrices characterized by that hydrolyzed cellulose that has been degraded by hydrolysis to a level that gives a sedimentation volume of 150–500 ml/10 g is mechanically treated by spheronization in a wet stage into spherical particles having a capacity of sorbing 1.5–9 times of their own weight of water and a tap bulk density of less than 0.85 g/ml in the dry state, whereupon a bioactive substance or bioactive substances in a solid, liquid or semiliquid form, are sorbed, precipitated or sublimized into the porous structure of the matrices in one or several steps, optionally with intermediate drying.

22. Process according to claim 21 characterized in that the porosity of the cellulose matrices is adjusted by degree of hydrolysis or by mechanical treatment to control the release of the bioactive substance.

23. Process according to claim 21 characterized in that the solid, liquid or semiliquid contain one or more release controlling materials in order to modify the release of the bioactive substance.

24. Process according to claim 23 wherein the material is selected from the group consisting of esters, ethers, alcohols and waxes.

25. Process according to claim 23 characterized in that the material is selected from the group consisting of cellulose derivatives, acrylic acid derivatives, hydrocarbons, carboxylic acids, and lipids.

26. Process according to claim 21 characterized in that the release of the bioactive substance or substances is modified by applying a release controlling material on the surface of the spherical particles.

27. Process according to claim 26 characterized in that the release controlling material is selected from the group consisting of cellulose derivatives, acrylic acid derivatives and co-polymers thereof, hydrocarbons, carboxylic acids, and lipids.

28. Process according to claim 26 wherein the release controlling material is selected from the group consisting of esters, ethers, alcohols and waxes.

29. Process for the preparation of tablets from porous cellulose matrices manufactured by mechanically treating hydrolyzed cellulose that has been degraded by hydrolysis to a level that gives a sedimentation volume of 150–500 ml/10 g by spheronization in a wet stage into spherical particles having a capacity of sorbing 1.5–9 times of their own weight of water and a tap bulk density of less than 0.85 g/ml in the dry state, whereupon said matrices are admixed, prior to compaction, with drags or drug-containing granules in order to improve the tabletting and tablet properties and thereafter compressed.

30. Process for the preparation of tablets according to claim 29 characterized by that said matrices with a size of 0.1–2.0 mm are admixed, prior to compaction, with drug-units of similar size which have been coated to modify the drug release properties, mask unpleasant taste or to improve the stability and thereafter compressed.

* * * * *